United States Patent [19]

Habets et al.

[11] Patent Number: 5,595,868
[45] Date of Patent: Jan. 21, 1997

[54] MONOCLONAL ANTIBODIES TO HEPATITIS C VIRUS

[75] Inventors: Winand J. A. Habets, Den Bosch; Miriam F. H. M. Klein-Rot, Wychen; Theodorus A. M. Oosterlaken, Boxtel, all of Netherlands; Sing H. Yap, Nieuwrode, Belgium

[73] Assignee: Akzo Nobel N.V., Arnhem, Netherlands

[21] Appl. No.: 514,982

[22] Filed: Aug. 14, 1995

Related U.S. Application Data

[63] Continuation of Ser. No. 237,958, May 3, 1994, abandoned, which is a continuation of Ser. No. 961,239, Oct. 15, 1992, abandoned.

[30] Foreign Application Priority Data

Oct. 15, 1991 [EP] European Pat. Off. .............. 91202659

[51] Int. Cl.⁶ ..................... G01N 33/569; G01N 33/576; A61K 39/29; C07K 16/08
[52] U.S. Cl. ................. 435/5; 435/7.1; 435/7.2; 435/70.21; 435/172.2; 435/240.27; 435/960; 435/975; 436/518; 436/536; 530/387.1; 530/388.1; 530/388.3
[58] Field of Search ..................... 436/536, 518; 435/240.27, 7.1, 7.2, 7.4, 172.2, 70.21, 5, 7.21, 960, 975; 530/387.1, 388.1, 388.3

[56] References Cited

U.S. PATENT DOCUMENTS 5,229,491 7/1993 Habets et al. ........................... 530/326

FOREIGN PATENT DOCUMENTS

| 0318216 | 5/1989 | European Pat. Off. | ......... C12N 15/00 |
| 0363025 | 4/1990 | European Pat. Off. | ......... C12N 15/51 |
| 0388232 | 9/1990 | European Pat. Off. | ......... C12N 15/51 |
| 0445801 | 9/1991 | European Pat. Off. | .......... C07K 7/04 |
| 0480041 | 4/1992 | European Pat. Off. | ......... C07K 15/12 |
| 9114705 | 3/1991 | WIPO | ............................ C07K 15/12 |

OTHER PUBLICATIONS

C. Trepo et al., "Non–A, non–B hepatitis virus: Identification of a core antigen–antibody system that cross reacts with hepatitis B core antigen and antibody," Journal of Medical Virology 8:1:31–47, Aug. 11, 1990.
Yap et al. J. Hepatology 20: 275–281 (1994).

*Primary Examiner*—Christina Chan
*Assistant Examiner*—Phillip Gambel
*Attorney, Agent, or Firm*—Mary E. Gormley

[57] ABSTRACT

The invention concerns a hybridoma cell line that produces a monoclonal antibody having binding specificity for epitopes on Hepatitis C virus (HCV) core protein and a monoclonal antibody produced by the hybridoma cell line as well.

5 Claims, No Drawings ial antibodies against HCV. This is presumably

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:1:

| Arg | Thr | Gln | Gln | Arg | Lys | Thr | Lys | Arg | Ser | Thr | Asn | Arg | Arg | Arg |
|---|---|---|---|---|---|---|---|---|---|---|---|---|---|---|
| 1 | | | | 5 | | | | | 10 | | | | | 15 |

MONOCLONAL ANTIBODIES TO HEPATITIS C VIRUS This is a continuation of U.S. patent application Ser. No. 08/237,958 filed May 3, 1994, now abandoned, which is a continuation of U.S. patent application Ser. No. 07/961,239, filed Oct. 15, 1992, now abandoned.

The invention relates to a hybridoma cell line that produces a monoclonal antibody having binding specificity for epitopes on Hepatitis C virus (HCV) core protein and a monoclonal antibody produced by the hybridoma cell line as well.

The invention also relates to a method for the detection of HCV in a sample and a test kit for carrying out said detection method.

BACKGROUND OF THE INVENTION

HCV has recently been recognized as one of the causative agents of NANB hepatitis (Non-A, Non-B). It can be distinguished from other forms of viral-associated liver diseases, including that caused by known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). Non-A, Non-B Hepatitis was first identified in transfused individuals. Transmission from man to chimpanzee and serial passage in chimpanzees provided evidence that Non-A, Non-B Hepatitis is due to a transmissible infectious agent or agents.

Epidemiologic evidence is suggestive that three types of Non-A, Non-B Hepatitis exist: the water-borne epidemic type; the blood or needle associated type; and the sporadically occurring (community acquired) type. However, the number of agents which may be the causative of Non-A, Non-B Hepatitis is still unknown.

Clinical diagnosis and identification of Non-A, Non-B Hepatitis has been accomplished primarily by exclusion of other viral markers. Among the methods used to detect putative Non-A, Non-B Hepatitis antigens and antibodies are agar-gel diffusion, counter-immunoelectrophoresis, immuno-fluorescence microscopy, immune electron microscopy, radioimmunoassay, and enzyme-linked immunosorbent assay. However, none of these assays has proved to be sufficiently sensitive, specific, and reproducible to be used as a diagnostic test for Non-A, Non-B Hepatitis. Recently serologic tests for HCV infection have been developed and are commercially available. However, for the development of a specific and sensitive method to enable a reliable diagnosis to be made in various phases of the infection, it is of great importance that HCV can be detected instead of the detection of antibodies directed against HCV as is carried out by the present commercially available tests.

It is self-evident that an early diagnosis of a putative patient infected with HCV will be of prime importance since as a consequence treatment of the patient suffering from the disease can start as early as possible.

BRIEF SUMMARY OF THE INVENTION

Prior to the present invention there has been no report of monoclonal antibodies generated against HCV. Although applications such as EP 318,216 and EP 388,232 state that monoclonal antibodies against HCV can be readily produced by one skilled in the art, in the year that has transpired since these publications, no one has yet disclosed the production of monoclonal antibodies against HCV. This is presumably due to lack of information of the three dimensional structure of the virus. No one skilled in the art till this moment will know the availability of the epitopes to bind antibodies. A hybridoma cell line has been produced by the fusion of a myeloma cell with a lymphocyte derived from a mouse previously inoculated with a HCV core peptide. This hybridoma produces a monoclonal antibody directed against a HCV core peptide.

DETAILED DESCRIPTION OF THE INVENTION

The monoclonal antibodies according to the present invention, therefore, provide a new means for the diagnosis of HCV infection.

In a preferred embodiment, the present invention provides a monoclonal antibody which has specificity for an epitope on Hepatitis C virus core protein wherein the monoclonal antibody is produced from a hybridoma cell line produced by the fusion of a myeloma cell with a lymphocyte derived from a mouse previously inoculated with a HCV core peptide.

In addition to this preferred embodiment, part of the invention is a monoclonal antibody directed against a HCV core peptide (A1327) with the amino acid sequence (SEQ ID NO:1) RTQQRKTKRSTNRRR (SEQ ID NO:2) or fragments thereof and analogous to the peptide and fragments thereof.

The monoclonal antibody with code HCV-OT 1F2 is produced by a hybridoma cell line. Said hybridoma cell line has been deposited by the European Collection of Animal Cell Cultures (ECACC) in Porton Down, U.K. under number: 91101711 at 17.10.91 under the terms and conditions of the Budapest Treaty, 1977.

The invention also comprises a method for the detection of HCV in a sample by contacting a sample with the above-described monoclonal antibody, whereafter the presence of immune complexes formed is detected and from this the presence of HCV in the sample is determined. A test kit to be used in an immunoassay is also part of the invention. Such a test kit contains at least a monoclonal antibody according to the invention.

The preparation of the hybridoma cell line producing the monoclonal antibodies according to the invention may occur by, for example, the Kohler and Milstein technique. So cell fusion, immortal antibody-producing cell lines can be created while also other techniques are avaiable such as direct transformation of B-lymphocytes with oncogenic DNA or transfection with Epstein-Barr Virus. The most preferred method is the Kohler and Milstein technique.

Kohler and Milstein are generally credited with having devised the techniques that successfully resulted in the formation of the first monoclonal antibody-producing hybridomas (G. Kohler and C. Milstein, 1975, Nature 256:495–497; 1976, Eur. J. Immunol. 6:511–519). By fusing antibody-forming cells (spleen lymphocytes) with myeloma cells (malignant cells of bone marrow primary tumors) they created a hybrid cell line, arising from a single fused cell hybrid (called a hybridoma or clone) which had inherited certain characteristics of both the lymphocytes and myeloma cell lines. Like the lymphocytes (taken from animals primed with sheep red blood cells as antigen), the hybridomas secreted a single type of immunoglobulin specific to the antigen; moreover, like the myeloma cells, the hybrid cells had the potential for indefinite cell division. The combination of these two features offered distinct advantages over conventional antisera. Whereas antisera derived from vaccinated animals are variable mixtures of polyclonal antibodies which never can be reproduced identically, monoclonal antibodies are highly specific immunoglobulins of a single type. The single type of immunoglobulin secreted by a hybridoma is specific to one and only one antigenic determinant, or epitope, on the antigen, a complex molecule having a multiplicity of antigenic determinants. For instance, if the antigen is a protein, an antigenic determinant may be one of the many peptide sequences (generally 6–7 amino acids in length; M. Z. Atassi, 1980, Molec. Cell. Biochem. 32:21–43) within the entire protein molecule. Hence, monoclonal antibodies raised against a single antigen may be distinct from each other depending on the determinant that induced their formation; but for any given clone, all of the antibodies it produces are identical. Furthermore, the hybridoma cell line is easily propagated and yields monoclonal antibodies in extremely high concentration.

After immunizing mice with synthetic, recombinant or natural HCV core antigen, preferably peptide A1327 as mentioned earlier, by using the above-mentioned hybridoma technique, it appears possible to obtain a hybridoma cell line producing a monoclonal antibody which has specificity for an epitope on Hepatitis C virus core protein.

Part of the invention is also the "humanizing" of the monoclonal antibodies in question. Techniques for raising the "humanized" monoclonal antibodies are known in the art.

The preparation of the peptide mentioned is effected adapting one of the known organic chemical methods for peptide synthesis or with the aid of recombinant DNA techniques. This latter method involves the preparation of the desired peptide by means of expressing a recombinant polynucleotide with a polynucleotide sequence which is coding for the peptide in question in a suitable microorganism as host.

The organic chemical methods for peptide synthesis are considered to include the coupling of the required amino acids by means of a condensation reaction, either in homogeneous phase or with the aid of the so-called solid phase.

As already previously indicated, the peptide in question can likewise be prepared with the aid of recombinant DNA techniques. This possibility is of importance particularly when the peptide is incorporated in a repeating sequence ("in tandem") or when the peptide can be prepared as a constituent of a (much larger) protein or polypeptide. For this purpose, as a constituent of a recombinant DNA, a polynucleotide is used which codes for the peptide.

The monoclonal antibodies according to the invention are extremely suitable to be used in immunoassays in order to detect HCV or HCV-fragments in a test sample. Depending on the nature and further characteristics of the monoclonal antibodies, the immunochemical reaction that takes place is a so-called sandwich reaction, an agglutination reaction, a competition reaction or an inhibition reaction.

Carrying out, for instance, a sandwich reaction for the detection of HCV in a test sample the test kit to be used comprises a monoclonal antibody according to the invention coated to a solid support, for example the inner wall of a microtest well, and either a labelled monoclonal antibody or fragment thereof as conjugate.

Supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle, a carrier protein such as BSA or KLH.

Labelling substances which can be used are, inter alia, a radioactive isotope, a fluorescent compound, an enzyme, a dye sol, metal sol or metal compound or other sol as sol particle.

As already mentioned monoclonal antibodies according to the invention are very suitable in diagnosis, while those antibodies which are neutralizing are very useful in passive immunotherapy. Also monoclonal antibodies may be used to raise anti-idiotype antibodies. Techniques for raising anti-idiotype antibodies are known in the art.

The anti-idiotype antibodies are also useful for prevention and/or treatment of Non-A, Non-B Hepatitis, as well as for the elucidation of important epitopic regions of HCV-antigens.

EXAMPLE

Preparation of monoclonal antibody HCV-OT 1F2, deposited by ECACC in Porton Down U.K. under nr.: 91101711, has been described earlier in this application.

In an effort to detect HCV antigen, the antibody reactivity of monoclonal antibodies by immunohistochemical staining on liver biopsy of a chimpanzee infected with NANB infectious agent(s) was investigated.

This chimpanzee had no serological markers of HBV, CMV and of EBV infection. In addition to HCV antibody sero-reactivity, the HCV RNA as detected by PCR using primers as described by Garson et al. (Lancet 336, 1022, 1990) was positive in sera and liver tissue.

Liver tissues were obtained at a time during which liver enzymes (ASAT-ALAT) were elevated.

Liver biopsy specimens were also obtained from:

10 patients with HCV infection (all were positive for HCV serologic markers and HCV-RNA) and 4 control patients consisted of:

2 patients with HBV infection
1 patient with PBC
1 patient with auto-immune chronic hepatitis.

All control patients were negative for HCV serological markers and for HCV-RNA as detected by PCR.

Immunohistochemistry:

Immunohistochemistry was performed on 4 μm thick cryostat sections of fresh frozen materials. The endogenous peroxidase activity was inhibited in a 0.3% $H_2O_2$ in methanol solution for 30 min at room temperature. The sections were then incubated with normal swine serum (1/20 for 7 min) at room temperature. The excess of swine serum was wiped off and the first specific monoclonal IgG (or rabbit antiserum or mouse antiserum) was applied for 30 min at room temperature. After rinsing in PBS (3×5 min), the slides were incubated with rabbit antiserum to mouse immunoglobulin (or goat antirabbit immunoglobulin) in a 1/20 PBS-NHS (10%) solution for 30 min at room temperature. After further rinsing in PBS (3×5 min), they were incubated with a soluble complex of horseradish peroxidase-rabbit anti-horseradish peroxidase (PAP, Dakopatts) for 30 min at room temperature in a 1/300 dilution. After washing, the peroxidase immuno-reaction product was developed in a diaminobenzidine (DAB)-$H_2O_2$ solution for 5 min at room temperature (60 mg of DAB was dissolved in 100 ml of PBS; after filtration, 100 μl of 30% $H_2O_2$ solution was added). After rinsing in tap water and differentiation in acid alcohol, the sections were mounted in DPX.

Results:

For the initial screening of antibodies for detection of HCV antigen in liver tissue, liver tissue obtained from chimpanzee infected with Non-A, Non-B Hepatitis was used.

Of the antibodies tested, the monoclonal antibody HCV-OT 1F-2 shows a "specific" cytoplasmic staining on this liver tissue.

All other antibodies react either "non specifically" or show no staining at all. The results of the 14 patients studied are given in table 1.

TABLE 1

Immuno-histochemical detection of HCV antigen in liver biopsies using monoclonal antibody HCV-OT 1F-2.

|  | Findings | |
| --- | --- | --- |
|  | positive | negative |
| 10 patients with Non-A, Non-B Hepatitis | 7 | 3 |
| 2 patients with Hepatitis B |  | 2 |
| 1 patient with PBC |  | 1 |
| 1 patient with auto-immune chronic Hepatitis |  | 1 |
| Total: | 7 | 7 |

This study provides convincing evidence that monoclonal antibody HCV-OT 1F-2 is able to detect specifically HCV antigen in cytoplasm of hepatocytes, despite the negative findings in three patients with Non-A, Non-B Hepatitis having positive serologic markers of HCV infection and in whom HCV-RNA was also detected in serum. The negative finding in these three patients may be due to a low concentration of viral antigen present in the hepatocytes or due to a relatively low sensitivity of the present assay for antigen detection. The immunologic specificity of the present assay was noted, since no reaction was found in liver tissues obtained from patients with hepatitis B and PBC. The reaction is consistent positive after an "immuno-absorption" with homogenate of normal human liver tissue.

We claim:

1. A hybridoma cell line obtainable from the European Collection of Animal Cell Cultures (ECACC) under accession number 91101711.

2. A monoclonal antibody produced by the hybridoma cell line of claim 1.

3. A method for the detection of HCV in a sample, which comprises: contacting said sample with a monoclonal antibody according to claim 2; detecting the presence of immune complexes formed; and thereby determining the presence of HCV in the sample.

4. A test kit for carrying out an immunoassay to detect HCV, comprising a monoclonal antibody according to claim 2 coated onto a solid support and a vial of said monoclonal antibody that has been labeled with a labelling substance.

5. A monoclonal antibody according to claim 2 coated onto a solid support.

* * * * *